United States Patent
Larson

(10) Patent No.: US 9,055,992 B2
(45) Date of Patent: Jun. 16, 2015

(54) DUAL MEDICAMENT CARPULE FOR DENTAL SYRINGES

(71) Applicant: Bryan Larson, North Salt Lake, UT (US)

(72) Inventor: Bryan Larson, North Salt Lake, UT (US)

( * ) Notice: Subject to any disclaimer, the term of this patent is extended or adjusted under 35 U.S.C. 154(b) by 0 days.

(21) Appl. No.: 14/106,555

(22) Filed: Dec. 13, 2013

(65) Prior Publication Data

US 2014/0170594 A1 Jun. 19, 2014

Related U.S. Application Data

(60) Provisional application No. 61/737,244, filed on Dec. 14, 2012.

(51) Int. Cl.
*A61M 5/24* (2006.01)
*A61C 19/08* (2006.01)
*A61M 5/28* (2006.01)
*A61M 5/19* (2006.01)

(52) U.S. Cl.
CPC .................. *A61C 19/08* (2013.01); *A61M 5/24* (2013.01); *A61M 5/283* (2013.01); *A61M 5/282* (2013.01); *A61M 5/285* (2013.01); *A61M 5/286* (2013.01); *A61M 5/284* (2013.01); *A61M 5/19* (2013.01)

(58) Field of Classification Search
CPC ........... A61M 5/24; A61M 5/28; A61M 5/31; A61M 5/00; A61M 5/282–5/286; A61M 5/19; A61M 5/2425; A61M 5/34
USPC ......... 604/191, 200, 201, 204, 214, 218, 232, 604/240, 244, 82–92; 433/90
See application file for complete search history.

(56) References Cited

U.S. PATENT DOCUMENTS

| | | | | |
|---|---|---|---|---|
| 2,193,322 A | * | 3/1940 | Lozier et al. | 604/88 |
| 3,678,931 A | | 7/1972 | Cohen | |
| 3,923,058 A | | 12/1975 | Weingarten | |
| 4,055,177 A | * | 10/1977 | Cohen | 604/88 |
| 4,439,184 A | | 3/1984 | Wheeler | |
| 4,573,972 A | * | 3/1986 | Kamstra | 604/191 |
| 4,702,737 A | | 10/1987 | Pizzino | |
| 4,792,329 A | | 12/1988 | Schreuder | |

(Continued)

FOREIGN PATENT DOCUMENTS

| | | |
|---|---|---|
| CA | 2728126 | 12/2009 |
| CN | 201618248 | 11/2010 |
| WO | WO 00/29051 | 5/2000 |

OTHER PUBLICATIONS

Allen L. Sisk, Vasoconstrictors in Local Anesthesia for Dentistry, 1992, Anesth. Prog., 39:187-193.*

(Continued)

*Primary Examiner* — Theodore Stigell
*Assistant Examiner* — Amber Stiles
(74) *Attorney, Agent, or Firm* — Pate Peterson PLLC; Brett Peterson

(57) ABSTRACT

A carpule for a dental syringe provides an internal piston disposed between a front septum and a rear plunger. The internal piston is hollow and includes a thin membrane front. The internal piston is designed to offer minimum resistance to movement in the carpule body to allow for aspiration and for easy dispensing. The internal piston divides the carpule into two anesthetic chambers, allowing an anesthetic without a vasoconstrictor and an anesthetic with a vasoconstrictor to be dispensed sequentially in a single injection and without causing undue trauma to the patient.

17 Claims, 8 Drawing Sheets

(56) References Cited

U.S. PATENT DOCUMENTS

| | | | |
|---|---|---|---|
| 4,861,335 | A | 8/1989 | Reynolds |
| 4,886,495 | A | 12/1989 | Reynolds |
| 5,069,670 | A | 12/1991 | Geprags et al. |
| 5,102,388 | A * | 4/1992 | Richmond ............ 604/88 |
| 5,137,511 | A | 8/1992 | Reynolds |
| 5,364,369 | A | 11/1994 | Reynolds |
| 5,637,087 | A | 6/1997 | Hofstetter |
| 5,665,068 | A | 9/1997 | Takamura |
| 5,788,670 | A | 8/1998 | Reinhard et al. |
| 5,935,101 | A | 8/1999 | Kakiuti et al. |
| 6,562,011 | B1 | 5/2003 | Buch-Rasmussen et al. |
| 6,723,074 | B1 | 4/2004 | Halseth |
| 6,764,471 | B2 | 7/2004 | Lee |
| 7,311,692 | B2 | 12/2007 | Kato et al. |
| 2002/0147430 | A1 | 10/2002 | Collins et al. |
| 2003/0199816 | A1 * | 10/2003 | Ramming ............ 604/89 |
| 2004/0106164 | A1 * | 6/2004 | Brown et al. ............ 435/14 |
| 2006/0178638 | A1 * | 8/2006 | Reynolds ............ 604/191 |
| 2006/0178644 | A1 | 8/2006 | Reynolds |
| 2007/0060876 | A1 | 3/2007 | Bassarab et al. |
| 2007/0142768 | A1 * | 6/2007 | Griffiths et al. ............ 604/82 |
| 2008/0015522 | A1 | 1/2008 | Yeshurun et al. |
| 2009/0326475 | A1 | 12/2009 | Carlyon |
| 2010/0262074 | A1 | 10/2010 | Seiferlein et al. |
| 2010/0274186 | A1 | 10/2010 | Seiferlein et al. |
| 2012/0265171 | A1 | 10/2012 | Thorne, Jr. et al. |

OTHER PUBLICATIONS

Allen L.Sisk, Vasoconstrictors in Local Anesthesia for Dentistry, 1992, Anesth. Prog., 39:187-193.*

International Search Report from related PCT/US2013/075179.

* cited by examiner

DUAL MEDICAMENT CARPULE FOR DENTAL SYRINGES

PRIORITY

The present application claims the benefit of U.S. Provisional Application Ser. No. 61/737,244, filed Dec. 14, 2012, which is herein incorporated by reference in its entirety.

THE FIELD OF THE INVENTION

The present invention relates to dental anesthetic. More particularly, the present invention relates to syringe and carpule systems for delivering dental anesthetic.

BACKGROUND

Syringes are used to deliver medication. For example, syringes are used to deliver anesthetic to patients' mouths before performing dental work. Many people dislike receiving injections. Receiving injections may cause anxiety and discomfort for the person which extends beyond the pain associated with being pierced by a needle and receiving the injection. Applicant thus desires to reduce the anxiety and discomfort associated with receiving injections and in particular to improve the patient experience with dental anesthetic.

BRIEF DESCRIPTION OF THE DRAWINGS

Non-limiting and non-exhaustive examples of the present invention are described with reference to the following figures, wherein like reference numerals refer to like parts throughout the various views unless otherwise specified.

Figure 1:
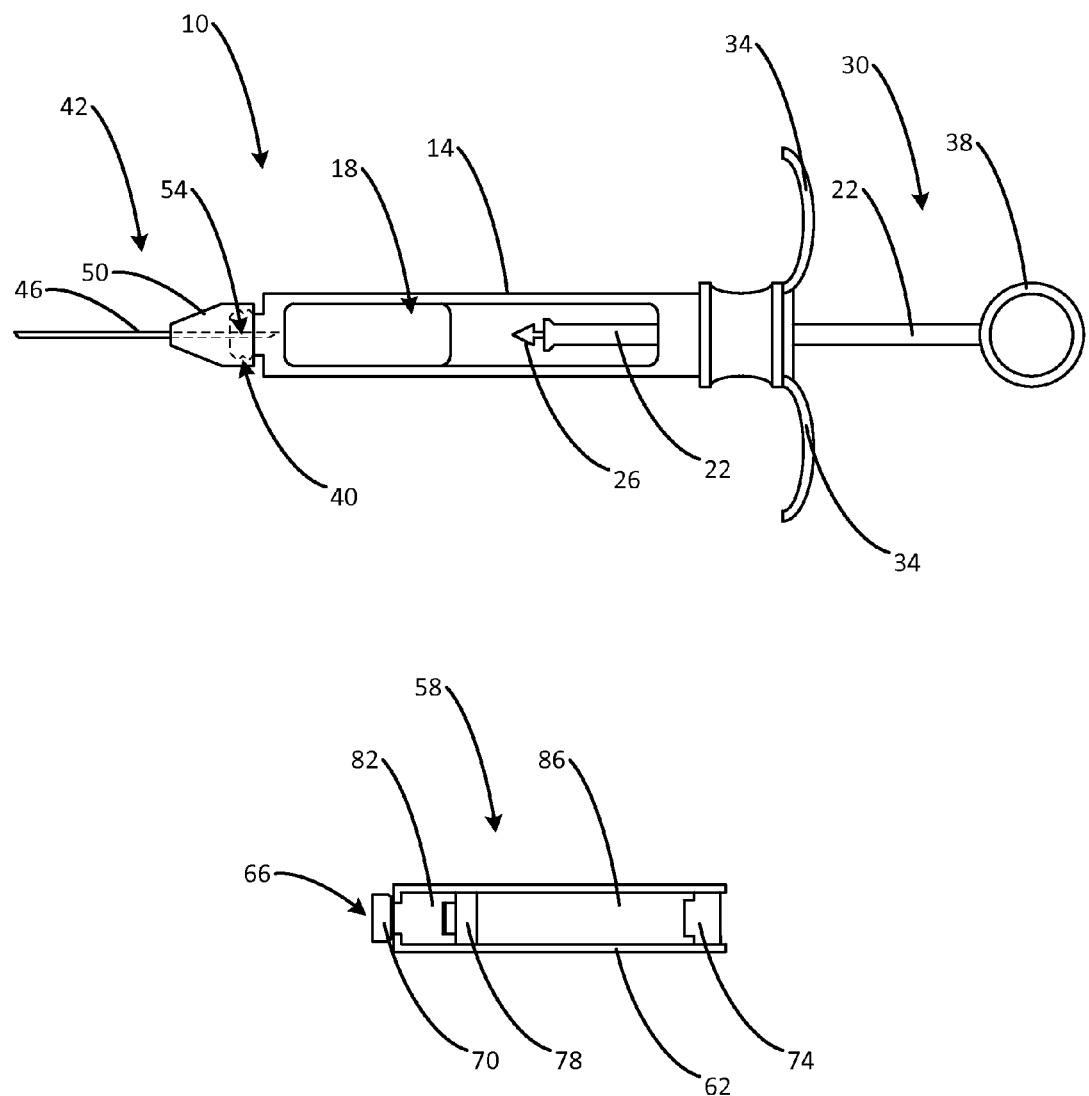
FIG. 1 shows a dental syringe and a carpule for the syringe.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various examples of the present invention. Also, common but well-understood elements that are useful or necessary in a commercially feasible embodiment are often not depicted in order to facilitate a less obstructed view of these various embodiments of the present invention.

It will be appreciated that the drawings are illustrative and not limiting of the scope of the invention which is defined by the appended claims. The examples shown each accomplish various different advantages. It is appreciated that it is not possible to clearly show each element or advantage in a single figure, and as such, multiple figures are presented to separately illustrate the various details of the examples in greater clarity. Similarly, not every example need accomplish all advantages of the present disclosure.

DETAILED DESCRIPTION

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

Reference throughout this specification to "one embodiment", "an embodiment", "one example" or "an example" means that a particular feature, structure or characteristic described in connection with the embodiment or example is included in at least one embodiment of the present invention. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

Embodiments in accordance with the present invention may be embodied as an apparatus or method. Accordingly, the present invention may take the form of an embodiment combining structural or method aspects that may all generally be referred to herein as a "system."

The disclosure particularly describes how to reduce patient pain and discomfort while administering anesthetic. Particularly, the present disclosure describes how a syringe and carpule system may be used to sequentially deliver different types of anesthetic.

Local anesthetic is frequently used for dental work such as fillings and the like. Typically, an anesthetic is applied to a region of the mouth by injecting the anesthetic into the soft tissue of the mouth with a syringe. Many local anesthetics used in dentistry, however, are vasodilators. These anesthetics cause dilation of blood vessels and an increase in blood flow in the area around the injection. This dilation of blood vessels removes the anesthetic from the injection area more quickly and reduces the effective duration of the anesthetic. These anesthetics are often unsuitable as they have insufficient duration for a dental procedure.

Some dental anesthetics contain epinephrine. The epinephrine is a vasoconstrictor and reduces blood flow in the anesthetized area, prolonging the effect of the anesthetic. Epinephrine, however, decomposes and requires a preservative to remain effective. The preservative causes the anesthetic to become acidic and causes pain on contact with tissue. Patients thus endure some pain until the anesthetic begins to function. This increases the discomfort and anxiety of the patient.

To decrease the pain, two different anesthetics may be used. A first anesthetic which does not contain a vasoconstrictor and preservative may be used. This first anesthetic may be used to numb the area even though the numbing effect may be short lived due to the dilating effect of the anesthetic. The first anesthetic may be used to numb the area sufficiently to allow the dentist to inject a second anesthetic with a vasoconstrictor and preservative. Many people, however, have an aversion to the syringe needle and would not want multiple injections even if it would decrease the pain and discomfort of the anesthetic.

Accordingly, a syringe system may be used which sequentially dispenses two different anesthetics in a single injection. In this manner, a dentist may dispense the first anesthetic, wait a moment if desired, and continue with dispensing the second anesthetic. All of this may be performed without withdrawing the syringe from the patient, minimizing the patient's discomfort with the procedure. A prefilled carpule may be provided which has a first anesthetic chamber and a separate second anesthetic chamber so that a dentist may dispense the two anesthetics sequentially.

Turning now to FIG. 1, a dental syringe and an anesthetic carpule are shown. The dental syringe 10 is reusable and the carpule 58 is disposable. The syringe 10 includes a syringe body 14 with an opening 18. The syringe body 14 may be tubular in nature, and may be formed from steel tube or rolled metal. The opening 18 is approximately the same width as the internal cavity of the syringe body 14. A syringe plunger 22 extends into the body 14 and is movable along the length of the body. The distal end of the plunger 22 includes a harpoon 26. The proximal end of the syringe 10 has a handle portion 30 which may include laterally extending flanges 34 forming finger grips which are attached to the body 14. The proximal end of the syringe 10 may include other types of finger grips. The syringe 10 also typically includes a thumb grip 38 attached to the plunger 22. The thumb grip 38 may be formed in a ring shape, allowing controlled aspiration and dispensing form the syringe 10. The handle portion 30 and thumb grip 38 allow a dentist to easily grasp and manipulate the syringe 10 during use. The distal end of the syringe 10 includes a needle adapter 40. The needle adapter 40 often is a threaded adapter to which a hypodermic needle 42 may be attached.

A needle 42 is attached to the distal end of the syringe body 14. The needle 42 may be disposable. The needle 42 includes an elongate and sharpened external hypodermic needle 46 (the injection end of the needle) formed of thin tubing, an attachment collar or hub 50, and a cartridge end 54 of the needle which is typically sharpened and which extends proximally from the needle hub 50. The cartridge end of the needle 54 and injection end of the needle 46 are often created from a single piece of hypodermic tubing to which a hub 50 is attached. Accordingly, the lumen of the injection end of the needle 46 is connected to the lumen of the cartridge end of the needle 54. The needle hub 50 may be threaded or have another fitting to allow the needle 42 to be removably attached to the needle adapter 40 on the distal end of the syringe body 14.

A carpule 58 contains anesthetic and is used with the syringe 10 to dispense anesthetic. A carpule 58 may be a prefilled and disposable anesthetic cartridge. A disposable carpule 58 provides sterility and convenience of use without excessive cost. The carpule 58 includes a hollow tubular glass body/cartridge 62. The distal end of the carpule body 62 is formed with a reduced diameter neck 64 and a circumferential ridge/bead 60 which is larger in diameter than the neck. The body 62 is closed at the distal end with a septum 66 and a crimped cap 70 attaching the septum to the body. The septum attaches to the distal face of the body 62 and the cap extends over part of the septum, and over the bead 60. The body 62 is tubular between the neck 64 and the proximal end of the body.

A silicone rubber plunger 74 is disposed in the bore of the body 62 and seals the proximal end of the body. The plunger 74 is typically made of an elastomeric material such as silicone, rubber, etc. An internal floating piston 78 divides the interior lumen/bore of the carpule body 62 into a first anesthetic chamber 82 and a second anesthetic chamber 86. The first anesthetic chamber 82 is located between the septum 66 and the piston 78 and the second anesthetic chamber 86 is located between the piston 78 and the plunger 74. The carpule 58 is typically provided prefilled with a first anesthetic in the first anesthetic chamber 82 and a second anesthetic in the second anesthetic chamber 86. In one example, the carpule 58 may be provided with a first medicine in the first chamber 82 and a second medicine in the second chamber 86. The first medicine may be an anesthetic and the second medicine may be a drug or vaccine, as an example.

In use, the carpule 58 is inserted through the opening 18 and into the interior of the syringe body 14. The opening 18 is slightly larger than the carpule 58 to allow the carpule to be loaded into the syringe. The harpoon 26 is inserted into the plunger 74 of the carpule 58. The harpoon 26 is typically barbed or hook shaped and becomes reliably engaged with the plunger 74 so that it is not accidentally withdrawn therefrom if the syringe is used for aspiration. The carpule 58 is placed at the forward/distal end of the syringe body 14. The septum 66 is pierced with the cartridge end 54 of the needle 42, causing the cartridge end 54 the needle 42 to pierce the septum 66 and enter the first anesthetic chamber 82.

Figure 2:
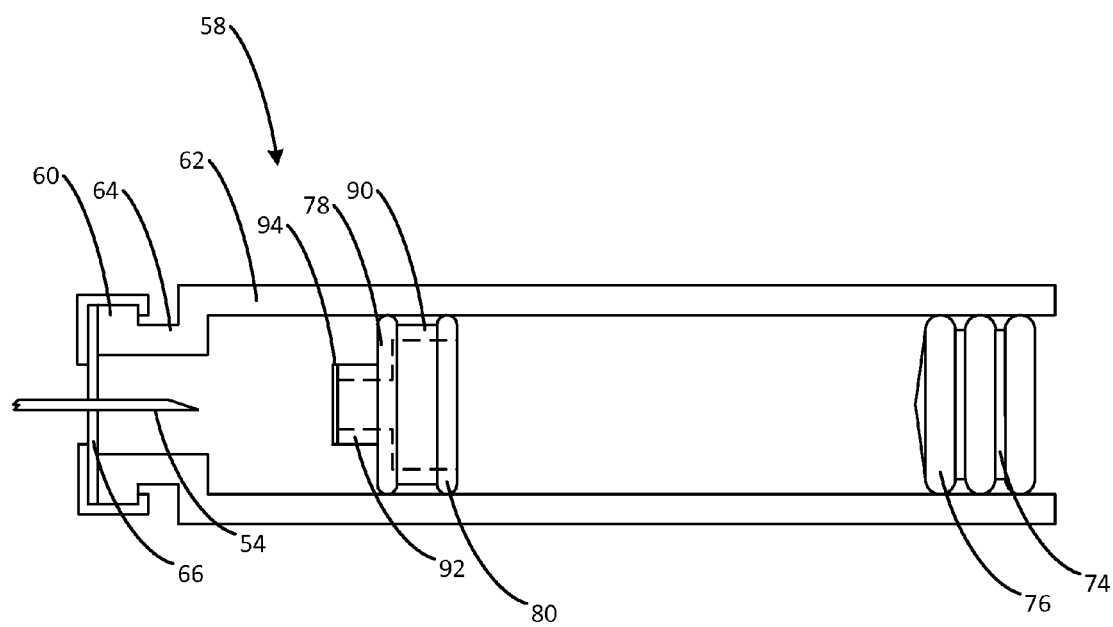
FIG. 2 shows a more detailed partially cut-away view of the carpule.

FIG. 2 shows an enlarged, partially cut-away drawing of the carpule 58 with some parts of the syringe showing. The cartridge end 54 of the needle 42 can be seen; illustrating how the cartridge end 54 of the needle may extend into the neck 64 of the carpule body 62. It can also be seen how the plunger 74 may be formed with ribs 76 to assist in sealing against the carpule body 62. Similarly, the piston 78 may be formed with ribs 80 to seal between the piston 78 and the carpule body 62.

Figure 3:
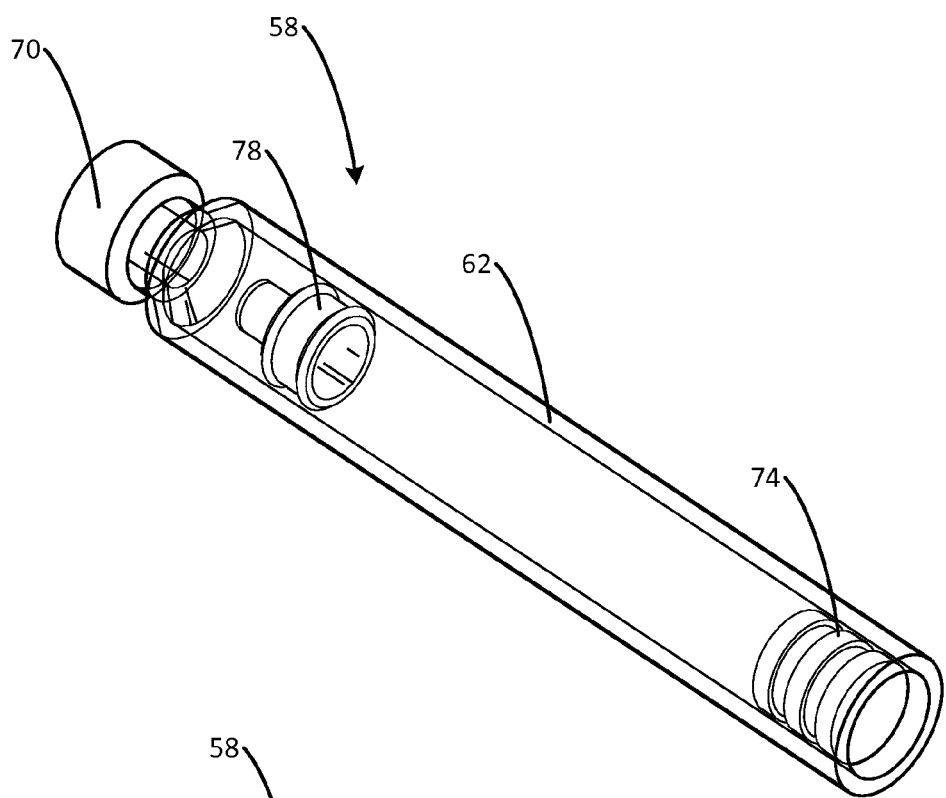
FIG. 3 shows a rear perspective view of the carpule.
Figure 4:
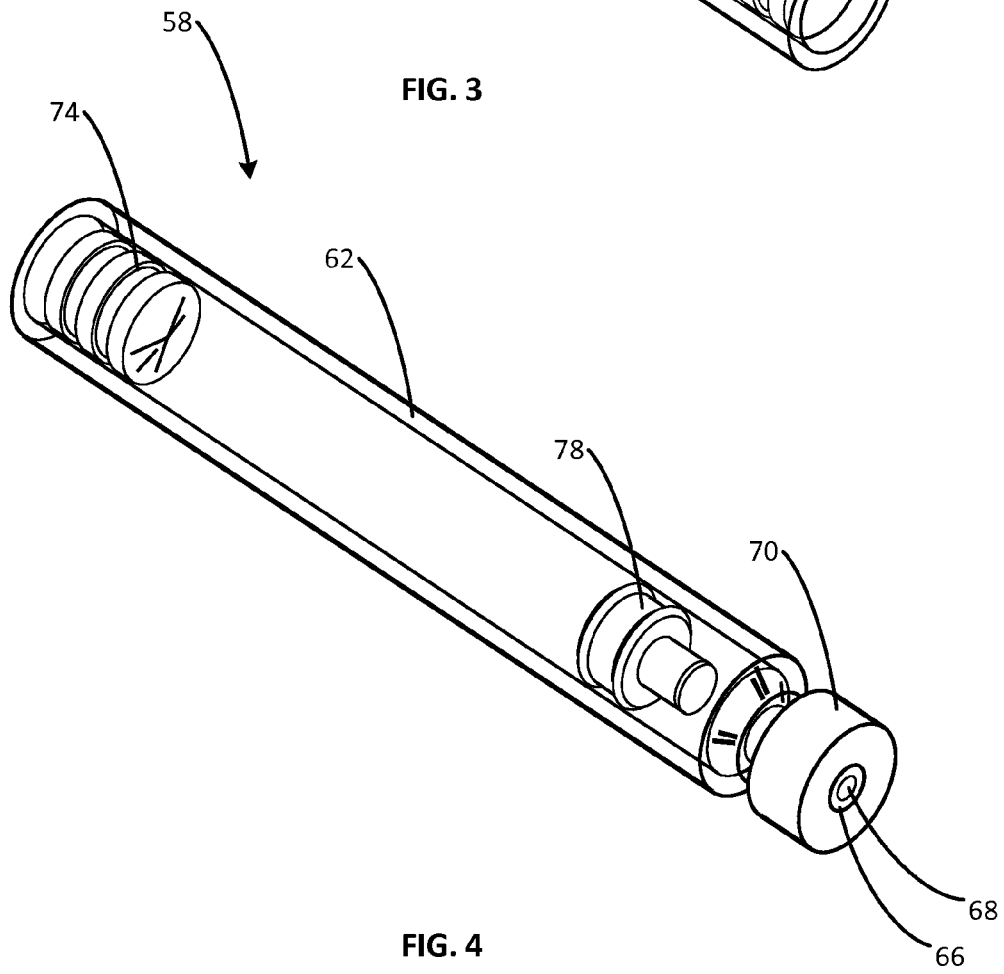
FIG. 4 shows a front perspective view of the carpule.

FIGS. 3 and 4 show perspective drawings of the carpule 58 and assist in visualizing the various structures and components discussed herein. FIG. 3 shows a rear perspective view of the carpule 58 and FIG. 4 shows a front perspective view of the carpule. As can be seen in FIG. 4, the center of the septum 66 may be marked with an indicator 68. The indicator 68 may be a small dot or circle, a raised ring, a small depression, a bump, etc. The indicator 68 may assist a user in piercing the center of the septum 66 with the cartridge end 54 of the needle 42 while assembling the syringe 10. This may reduce the likelihood of any malfunction while dispensing anesthetic from the carpule 58.

Figure 5:
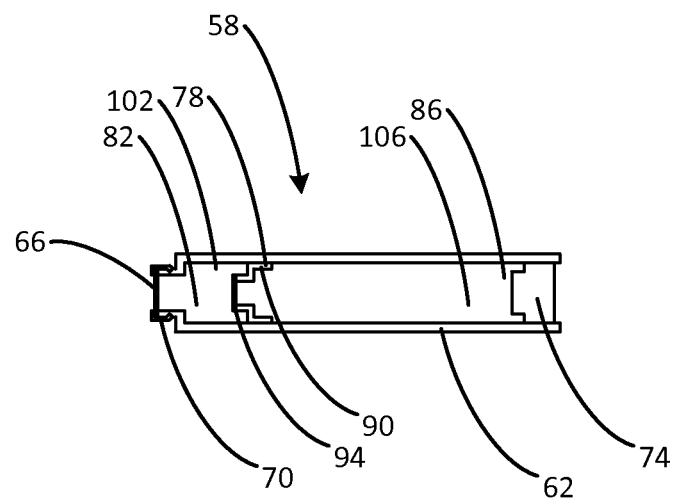
FIGS. 5 through 11 show cross sectional views of the carpule.

FIG. 5 shows the carpule 58 in cross section. The plunger 74 is cylindrical and has an outer diameter slightly larger than the bore of the body 62 so that the plunger seals against the bore. In some examples, ribs 76 maybe formed around the outside of the larger body portion of the plunger to assist in sealing against the body bore and to permit smooth movement of the plunger 74 within the body 62. Some features such as the ribs 76 shown in FIG. 2 are not shown in other figures in order to not obscure the clarity of the drawings. If desired, the distal end of the plunger 74 may be formed with a reduced diameter or with a tapering or conical shape. This may be useful in allowing the carpule 58 to be filled without retaining air bubbles. Although not necessary, the distal end of the plunger 74 may taper in size or be otherwise shaped to nest somewhat into the proximal end of the piston 78. The proximal end of the plunger 74 is typically flat, allowing the plunger 74 to receive the harpoon 26. The plunger 74 is often made of an elastomer and is typically solid. The plunger 74 is sufficiently soft to receive the harpoon 26.

The septum 66 is relatively thin and is often made of rubber which may be easily pierced by the needle 42 and reliably seal against the needle during use. The septum 66 is held against the front of the body 62 by the crimped on cap 70. Additionally, adhesive may be used to seal the septum against the body 62. As can be seen in FIG. 4, the septum 66 may be manufactured with a marking 68 such as a small depression, a raised circle, a printed circle, a printed center dot or cross, etc. to assist a person with placing the needle 42 (the cartridge end 54 of the needle in particular) through the center of the septum. Placing the needle 42 through the septum 66 closely to the center may ensure that the piston 78 functions properly as described.

The piston 78 is generally hollow. The piston 78 may be formed from a body portion 90 and a membrane 94. The body portion 90 of the piston 78 may be formed from a sufficiently rigid elastomer or a polymer or plastic material, allowing the body portion to be structurally sound while allowing a hollow interior. The body portion 90 is generally cylindrical with a hollow interior and may have a protruding distal end 92 with a reduced diameter to nest within the distal end (neck 64) of the carpule body 62. In many examples, the cartridge end 54 of the needle 42 extends sufficiently to pierce the cartridge septum 66, but does not extend into the main portion of the body 62 of the carpule. As such, the membrane 94 may need to move into the neck of the carpule 58 as the first anesthetic is dispensed, allowing the cartridge end 54 of the needle 42 to pierce the membrane 94 and allow the second anesthetic to be dispensed. Accordingly, the distal end 92 of the piston 78 may be cylindrical and hollow and may be formed with an outer diameter which is less than the inner diameter of the neck 64 of the carpule body 62.

Thus, the piston 78 may have a proximal body portion which is cylindrical and which is slightly larger in diameter than the bore of the carpule body 62 and a distal body portion which is a smaller diameter. The proximal and distal body portions of the piston 78 are hollow and are open from the proximal end of the piston 78 up to the membrane 94. The proximal and distal body portions are of sufficient annular thickness to support the shape of the piston and to seal against the bore of the carpule body 62. Thus, the body portion of the piston 78 may have cylindrical walls which are between about 0.015 and about 0.04 inches thick (between about 0.3 mm and 1 mm), and more commonly between about 0.02 and about 0.03 inches thick (between about 0.5 mm and 0.75 mm). The body 90 of the piston 78 may have ribs (80, FIG. 2) which assist in sealing against the bore of the carpule body 62. These ribs may often be between about 0.001 and about 0.02 inches tall and wide (between about 0.025 mm and 0.5 mm), and may more commonly be between about 0.01 and 0.015 inches tall and wide (between about 0.25 mm and 0.35 mm). The use of ribs 80 may improve the sealing while permitting smooth sliding movement of the piston 78.

The ribs 80 may thus extend circumferentially around the outer diameter of the piston 78. These ribs provide a slight interference fit with the internal bore of the carpule body 62 to seal between the piston 78 and the body. The amount of interference is small, and in some examples, the ribs may be between about 0.002 and about 0.004 inches (between about 0.05 mm and 0.1 mm) larger in diameter than the bore of the carpule body 62. The amount of interference is small so that the piston 78 does not provide significant resistance to movement and does not create any significant pressure differential across the membrane 94.

The body 90 of the piston 78 may be formed from a polymer, thermoplastic, thermoplastic elastomer, etc. In on example, the body 90 of the piston may be formed from a composite of two materials. The body 90 may be formed from a rigid thermoplastic or thermoplastic elastomer with ribs overmolded or otherwise formed from a softer elastomer or thermoplastic elastomer. This may allow the body 90 to have sufficient structural strength while remaining hollow and may allow the body/ribs to seal against the bore of the carpule body 62 reliably without causing undue resistance to the piston 78 sliding within the bore of the carpule body 62.

The distal face of the piston 78 is formed by a membrane 94. The membrane 94 may be formed from a thin rubber or silicone, a thin plastic/polymer, a film such as Mylar, etc. In one example, the membrane 94 may be formed from Mylar, a polyolefin such as polyethylene or polypropylene, a metal foil such an aluminum foil, etc. The membrane 94 may be between about 0.0001 and about 0.025 inches thick (between about 0.002 mm and 0.65 mm), and may typically be between about 0.0001 and 0.01 inches thick (between about 0.002 mm and 0.2 mm), or between about 0.005 and about 0.01 inches thick (between about 0.1 mm and 0.2 mm). As such, the membrane 94 typically does not provide significant strength to the internal piston 78 and the body 90 of the piston 78 typically must provide all of the strength. More importantly, the membrane 94 does not provide a significant resistance to puncture. As such, the membrane 94 is easily punctured by the cartridge end 54 of the needle 42 when moved against the needle. The membrane 94 may often be glued or heat sealed to the body 90 of the internal piston 78. The body 90 and membrane 94 may be made as a one piece structure in some configurations. The body 90 and membrane 94 together form a sealed and non-permeable piston that prevents fluid from the first anesthetic chamber 82 from mixing with fluid in the second anesthetic chamber 86.

Figure 6:
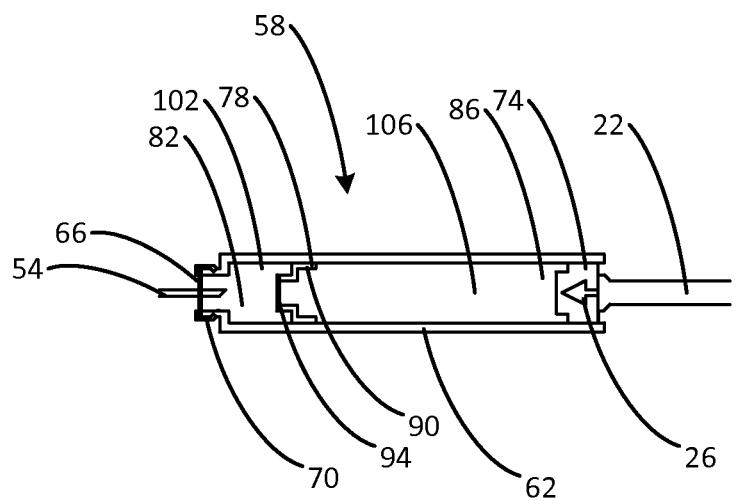

FIG. 6 also shows the carpule 58 in cross section. The carpule 58 has been placed into the syringe 10 and the harpoon 26 has been inserted into the plunger 74. As shown, the cartridge end 54 of the needle 42 is inserted through the carpule septum 66 and the needle 42 is attached to the needle adapter 40. As seen, the cartridge end 54 of the needle 42 often does not extend beyond the distal neck of the carpule 58. In this situation, the distal end 92 of the piston 78 should be reduced in diameter so that it can move into the carpule neck and the cartridge end 54 of the needle 42 can pierce the membrane 94.

Figure 7:
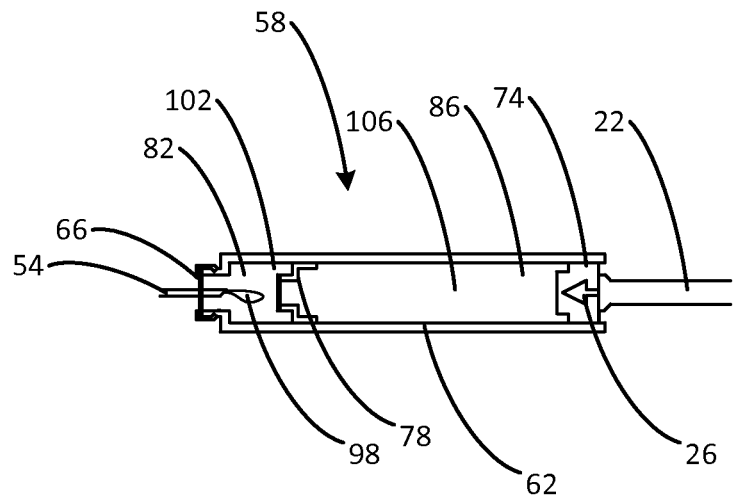

In use, the harpoon 26 allows the plunger 74 to be moved distally in the carpule to dispense anesthetic and proximally in the carpule to aspirate. FIG. 7 illustrates the use of the carpule 58 in aspiration. When the injection end 46 of the needle 42 is placed into the patient for an injection, the plunger 22 may be withdrawn slightly to aspirate or cause a reduced pressure within the carpule 58. This will show if the needle 42 is placed in a blood vessel as, in such a location, a small amount of blood 98 is drawn into the carpule 58 through the needle 42. The freely moving internal piston 78 allows a dentist to do so as it does not provide sufficient resistance to movement which would make this task more difficult. To ensure that aspiration with the carpule 58 is possible, it is typically desirable that the piston 78 will move freely within the bore of the carpule body 62 with an applied pressure of 10 psi or less. More preferably, the piston 78 will move freely within the carpule body 62 under a pressure of 5 psi or less. After the aspiration check demonstrates that the needle 46 is properly positioned (i.e. not within a blood vessel), the dentist may proceed to dispense anesthetic.

The carpule 58 may include a first anesthetic 102 without a vasoconstrictor in the first anesthetic chamber 82 and may include a second different anesthetic 106 with a vasoconstrictor and preservative in the second anesthetic chamber 86. In one example, the first anesthetic chamber 82 may be filled with an anesthetic 102 such as prilocaine (such as a 4 percent solution of prilocaine), lidocaine (such as a 2 percent solution), or mepivicaine (such as a 3 percent solution) without a vasoconstrictor or a preservative. The second anesthetic chamber 86 may be filled with a suitable anesthetic 106 such as lidocaine or articaine with a vasoconstrictor such as epinephrine or norepinephrine and a preservative. The first anesthetic chamber 82 may contain a smaller volume of anesthetic than the second anesthetic chamber 86. In one example, the first anesthetic chamber 82 may contain between about 10 percent and about 35 percent of the volume of the carpule 58 with the second anesthetic chamber 86 containing between about 65 percent and about 90 percent of the volume of the carpule 58. In another example, the first anesthetic chamber 82 may contain between about 20 percent and about 25 percent of the volume of the carpule 58 with the second anesthetic chamber 86 containing between about 75 percent and about 80 percent of the volume of the carpule 58.

Figure 8:
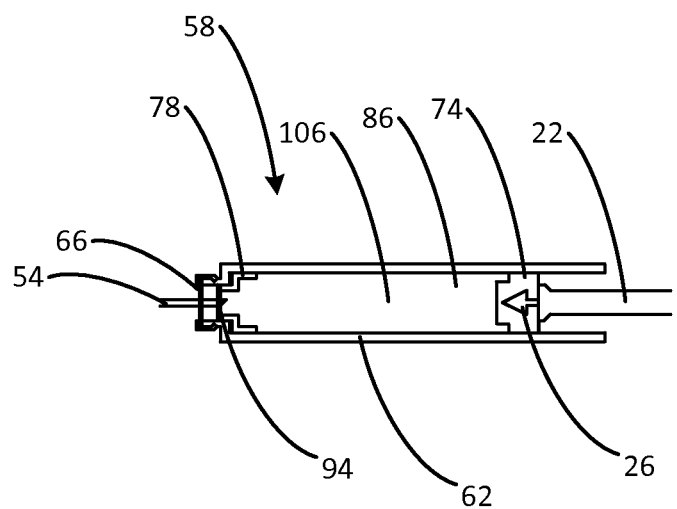

FIG. 8 shows the carpule 58 while dispensing anesthetic therefrom. The plunger 74 is moved distally (by moving the syringe plunger 22) to dispense some of the first anesthetic 102 from the first anesthetic chamber 82 after placing the injection end 46 of the needle 42 in a desired location within the patient. The first anesthetic 102 is typically an anesthetic without a vasoconstrictor such as prilocaine. This anesthetic 102 allows the dentist to numb an area of the patient's mount with an anesthetic which does not cause pain. The dentist may thus slowly dispense some or all of the first anesthetic 102 and then wait for a few seconds for the first anesthetic 102 to take effect before dispensing the second anesthetic 106. The complete injection may be performed without withdrawing the needle and puncturing the tissue a second time.

Where the first anesthetic 102 does not have a vasoconstrictor, it may have a shorter useful duration than the second anesthetic 106. As such, it may not contribute as much to the available time to perform a dental procedure. The volume of the first anesthetic 102 is thus often minimized; providing only a sufficient amount of first anesthetic 102 to numb an area of the patient's mouth sufficiently that the patient does not feel pain upon introduction of the second anesthetic 106. In one example, the second anesthetic 106 may have a somewhat higher amount of vasoconstrictor than would be otherwise used to offset the amount of vasoconstrictor not present in the first anesthetic 102. In this example, the vasoconstrictor may achieve a desired reduction in blood flow to prolong the effectiveness of the first anesthetic 102 and second anesthetic 106 and provide sufficient duration.

As shown, the piston 78 moves forwards as the first anesthetic 102 is dispensed. The advancement of the plunger 74 displaces the second anesthetic 106, causing movement of the piston 78 and displacement of the first anesthetic 102. The first anesthetic 102 is dispensed and the piston 78 is advanced until the membrane 94 is pressed against the cartridge end 54 of the needle 42 and punctured thereby. The membrane 94 is thin and easily pierced by the end of the needle 42. As such, piercing the membrane 94 with the end 54 of the needle 42 requires minimal force and provides minimal pressure change or disruption to the position of the syringe 10 and movement of the plunger 22. This assists in the prevention of pain and trauma to the injection site from the rapid tissue expansion which may occur if the piston 78 were more difficult to pierce and a greater amount of force against the plunger 74 was required, as the additional applied force would quickly dispense a volume of anesthetic once the piston 78 was pierced.

Once the cartridge end 54 of the needle 42 pierces the membrane 94, the second anesthetic chamber 86 and second anesthetic 106 are exposed to the needle lumen and available for dispensing into the patient. The dentist will typically dispense the first anesthetic 102 slowly and wait a short period of time to allow the patient's mouth to become numb. At this point, the patient will not feel discomfort while the dentist dispenses the second anesthetic 106 which typically contains a vasoconstrictor and preservative. The vasoconstrictor may promote the longevity of both the first anesthetic 102 and the second anesthetic 106.

Figure 9:
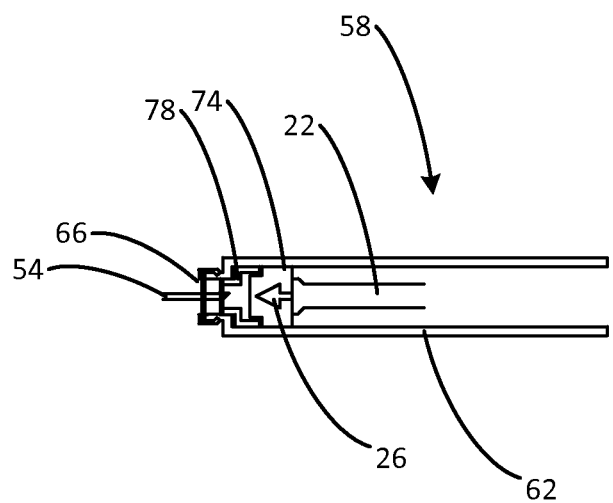
Figure 10:
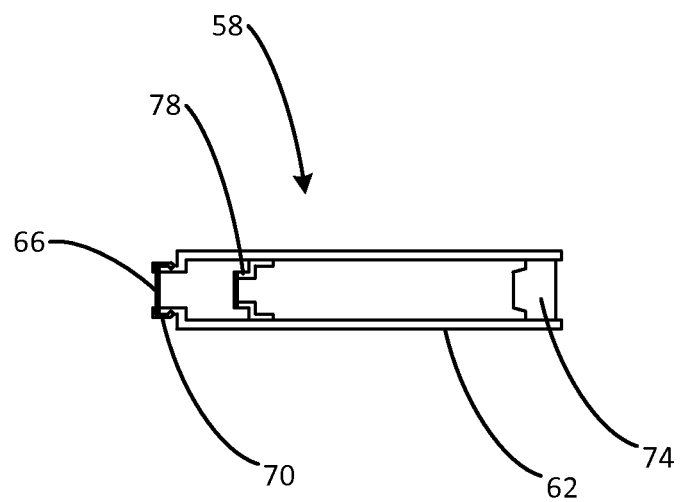
Figure 11:
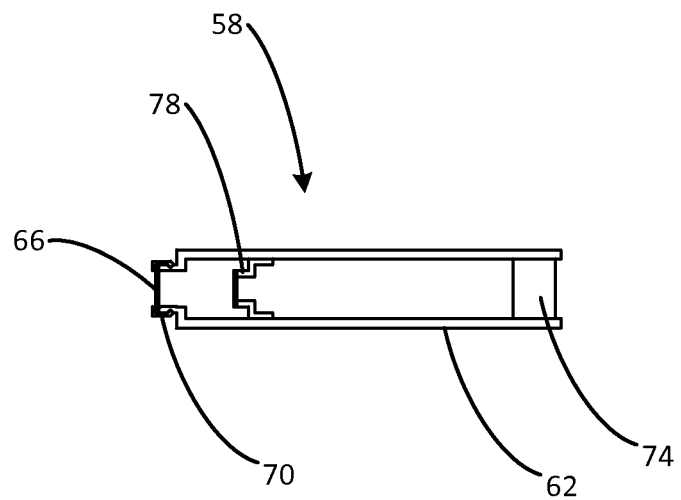

As shown in FIG. 9, the plunger 74 may be move distally in the carpule 58 to dispense the second anesthetic 106 therefrom. The second anesthetic 106 may be dispensed from the carpule 58 until the plunger 74 is contacting the piston 78 and the piston 78 is contacting the neck 64 or distal end of the carpule body 62. At this point, no further anesthetic may be dispensed.

Although some anesthetic capacity is lost in the carpule 58 due to the presence of the piston 78, the loss in capacity is small. The carpule 58 may be about 2.5 inches long (about 63 mm) and the larger proximal portion of the piston body 90 may be about ⅛ of an inch long. This scenario would provide a carpule 58 with a loss of approximately 5 percent or less of anesthetic volume.

Various processes may be used to fill or otherwise manufacture a carpule 58. By way of example, one process may begin with an empty glass carpule body 62 with the open proximal end facing up. The piston 78 may be inserted into the body 62 such that the depth from the proximal end of the body to the piston 78 allows for the desired total volume of second anesthetic solution 106 in the second chamber 86. That is to say that the piston 78 may be placed at a location in the carpule body 62 where the volume in the carpule body lumen/bore between the piston 78 and the proximal end of the carpule body 62 is equal to the desired volume of second anesthetic 106. The second anesthetic chamber 86 (the proximal portion of the carpule body 62) may then be filled to the top with the desired second anesthetic solution 106. The plunger 74 may then be inserted into the proximal end of the carpule body 62. Inserting the plunger 74 will displace the second anesthetic solution 106 in the second anesthetic chamber 86 and move the piston 78 distally as the plunger 74 is pressed in place. This may be accomplished such that there is no air trapped in the second chamber 86.

As is shown in FIGS. 1, 2, 4, 10, and 11, the distal end of the plunger 74 may be manufactured with a flat distal face of with a protruding nub, point, cone, etc. The distal protrusion may be formed with a slight taper, such as a 6-8 degree taper, or with a relatively short and steeply sloped conical shape to encourage air bubbles to move away from the plunger 74 and out of the body 62 when inserting the plunger into the body 62. Air bubbles may tend to move around the plunger 74 and escape from the second anesthetic chamber 86 rather than becoming trapped against a flat distal face of a plunger 74. Alternatively, a flat face may be easily used by filling anesthetic into the carpule body until the surface of the anesthetic liquid is level with or slightly above the proximal end of the carpule body 62. After the plunger 74 is inserted to the desired depth, the second anesthetic chamber 86 is closed and sealed.

The carpule 58 may then be inverted so that the distal end of the body 62 is facing up. The remaining empty volume inside of the body 62 will now reflect the desired volume of anesthetic solution 102 to be placed in the first anesthetic chamber 82. The first anesthetic chamber 82 may be filled with the desired first anesthetic solution 102, such as prilocaine. The first anesthetic chamber 82 is typically filled to the distal end of the carpule body 62 and any bubbles are removed from the first anesthetic chamber 82. A septum 66 may then be placed on the distal end of the carpule 58 without trapping air bubbles in the carpule 58 and the septum 66 may be sealed to the body 62 if necessary. A collar/cap 70 may be crimped in place around the septum 66 and the distal ridge 60 and neck 64 of the carpule body 62. In this manner, the carpule 58 may be filled without trapping air bubbles in the carpule. If desired, the carpule 58 may be filled or treated under vacuum conditions to assist in eliminating bubbles from the carpule. The carpule 58 may then be sterilized and packaged for use.

Figure 12:
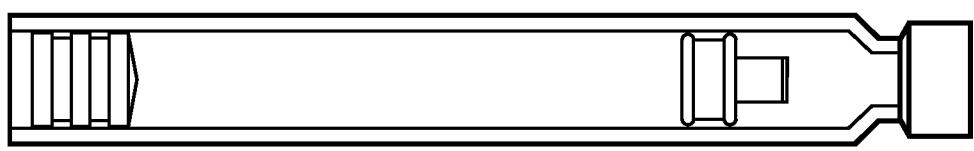
FIG. 12 shows a side view of the carpule.
Figure 13:
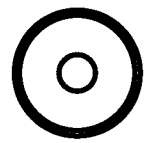
FIG. 13 shows a front view of the carpule.
Figure 14:
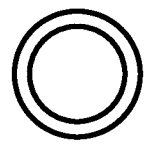
FIG. 14 shows a back view of the carpule.

FIG. 12 shows a side view of the carpule 58. As the carpule is typically round and symmetrical, this view also shows the left and right sides and the top and bottom sides of the carpule. FIG. 13 shows a front view of the carpule. FIG. 14 shows a back view of the carpule.

The carpule 58 is advantageous as it allows for minimizing pain and damage to a patient's mouth during application of anesthetic. The patient is able to receive a long lasting anesthetic without the stinging or unpleasant feeling which is typically associated with the anesthetic. The dentist is able to accomplish a comfortable and long lasting anesthesia in a smooth and easy manner which does not require multiple injections. Additionally, the carpule 58 is compatible with existing dental syringes. No change in equipment is required to implement, distribute, and use the carpule 58. The techniques for dispensing anesthetic from the carpule 58 are sufficiently similar to those techniques already used by dentists and minimal training is necessary to use the carpule.

The above description of illustrated examples of the present invention, including what is described in the Abstract, are not intended to be exhaustive or to be limitation to the precise forms disclosed. While specific examples of the invention are described herein for illustrative purposes, various equivalent modifications are possible without departing from the broader scope of the present claims. Indeed, it is appreciated that specific example dimensions, materials, voltages, currents, frequencies, power range values, times, etc., are provided for explanation purposes and that other values may also be employed in other examples in accordance with the teachings of the present invention.

What is claimed is:

1. A dental carpule comprising:
   a tubular carpule body having a cylindrical bore along a length thereof, the carpule having a neck formed on a distal end thereof and a hole formed through the neck which is smaller in diameter than the bore and which connects the bore to a distal face of the carpule body;
   a septum fixedly attached to the distal face of the carpule body to close the distal end of the carpule body;
   a plunger disposed in a proximal end of the bore such that the plunger seals against the bore to close the proximal end of the bore;
   a piston disposed in the bore between the septum and the plunger such that the piston divides the bore into a first anesthetic chamber and a second anesthetic chamber, wherein the piston comprises a generally cylindrical piston body having a hole therethrough, the hole being disposed in alignment with the bore of the carpule body and a membrane which is thin compared to a cylindrical wall of the piston body and which is attached to a distal face of the piston body to close the hole through the piston body;
   wherein the piston comprises a proximal body portion which is cylindrical and which seals against the carpule body bore and a generally cylindrical distal body portion extending distally from the proximal body portion which is smaller in diameter than the proximal body portion and which is smaller in diameter than the hole through the carpule body neck;
   a first anesthetic without a vasoconstrictor disposed in the first anesthetic chamber; and
   a second anesthetic with a vasoconstrictor disposed in the second anesthetic chamber.

2. The carpule of claim 1, wherein the piston comprises ribs formed around the piston body to seal against the carpule body bore.

3. The carpule of claim 1, wherein the membrane is formed from a different material than the piston body.

4. The carpule of claim 1, wherein the cylindrical wall of the piston body has a thickness which is multiple times thicker than a thickness of the membrane.

5. A system comprising the carpule of claim 1, wherein the carpule is inserted into a syringe for use, and wherein an injection needle is attached to the syringe such that a cartridge end of the needle pierces the septum, and wherein the cartridge end of the needle does not extend proximally in the carpule body beyond the neck.

6. The carpule of claim 1, wherein the piston body is generally rigid.

7. The carpule of claim 1, wherein the piston is movable to a distal end of the bore and is prevented from moving further distally at the distal end of the bore, and wherein the bore is smooth along its length to the distal end.

8. A dental system comprising:
   a dental carpule comprising:
      a tubular carpule body having a cylindrical bore along a length thereof, the carpule having a neck formed on a distal end thereof and a hole formed through the neck which is smaller in diameter than the bore and which connects the bore to a distal face of the carpule body;
      a septum fixedly attached to the distal face of the carpule body to close the distal end of the carpule body;
      a plunger disposed in a proximal end of the bore such that the plunger seals against the bore to close the proximal end of the bore;
      a piston disposed in the bore between the septum and the plunger such that the piston divides the bore into a first anesthetic chamber and a second anesthetic chamber, wherein the piston comprises a generally cylindrical piston body having a hole therethrough, the hole being disposed in alignment with the bore of the carpule body and a membrane which is thin compared to a cylindrical wall of the piston body and which is attached to a distal face of the piston body to close the hole through the piston body;
      a first anesthetic without a vasoconstrictor disposed in the first anesthetic chamber; and
      a second anesthetic with a vasoconstrictor disposed in the second anesthetic chamber;
   wherein the carpule is inserted into a syringe for use, and wherein an injection needle is attached to the syringe such that a cartridge end of the needle pierces the septum, and wherein the cartridge end of the needle does not extend proximally in the carpule body beyond the neck; and
   wherein the membrane is smaller than the hole through the carpule neck and wherein, during use, the piston is displaced distally while dispensing the first anesthetic until the membrane passes into the carpule neck and the membrane is pierced by the cartridge end of the needle.

9. The system of claim 8, wherein, after the membrane is pierced by the needle, further distal advancement of the plunger dispenses the second anesthetic through the needle.

10. The carpule of claim 1, wherein the septum comprises an indicator mark on the center of a distal face of the septum.

11. A carpule comprising:
    a tubular carpule body having a cylindrical bore disposed along a length thereof;
    a septum fixedly attached to a distal end of the carpule body to seal the distal end of the carpule body;
    a plunger disposed in a proximal end of the bore such that the plunger seals against the bore to close the proximal end of the bore;

a generally rigid piston disposed in the bore between the septum and the plunger such that the piston divides the bore into a first medicine chamber and a second medicine chamber;

wherein the piston comprises a generally cylindrical piston body having a hole therethrough, the hole being disposed in alignment with the bore of the carpule body, and a membrane attached to a distal face of the piston body to close the hole through the piston body, the hole extending through the piston body to expose a proximal face of the membrane;

wherein the piston more specifically comprises a generally cylindrical proximal piston body, a shoulder disposed at the distal end of the proximal piston body, and a generally cylindrical distal body section which has a diameter which is smaller than a diameter of the proximal piston body and which protrudes distally from the shoulder, and wherein the distal body section is nestable within a reduced diameter carpule body neck which extends distally from the bore, and wherein the membrane is attached to a distal face of the distal body section;

a first medicine disposed in the first medicine chamber; and a second medicine different than the first medicine disposed in the second medicine chamber.

12. The carpule of claim 11, wherein the piston is movable to the distal end of the bore and is prevented from moving further distally at the distal end of the bore, and wherein the distal end of the bore is smooth.

13. A system comprising the carpule of claim 11, wherein, during use of the carpule, a needle is inserted through the septum and into the carpule body such that the needle remains in the carpule body neck, the plunger is advanced, causing advancement of the piston and dispensing of the first medicine until the membrane is pushed into the carpule body neck and against the needle and the needle punctures the membrane, and subsequent advancement of the plunger dispenses the second medicine.

14. A carpule comprising:

a carpule body having a bore along a length thereof;

a pierceable seal attached to a distal end of the carpule body to close a distal end of the bore;

a plunger disposed in a proximal end of the bore to close the proximal end of the bore, the plunger being slidable within the bore;

a piston disposed in the bore between the seal and the plunger, the piston sealing against the bore to divide the bore into a first medicine chamber and a second medicine chamber;

wherein the piston comprises a cylindrical body, a membrane disposed on a distal end of the cylindrical body, and an opening in a proximal end of the cylindrical body, the opening extending distally to the membrane such that the membrane is exposed to the proximal end of the piston;

wherein the distal end of the carpule body has a neck having a reduced diameter hole therethrough and wherein a distal portion of the piston body is generally cylindrical and has a reduced diameter which permits the distal portion of the piston body and the membrane to extend into the carpule body neck;

wherein the piston has a range of distal movement which terminates adjacent a distal end of the bore, and wherein the bore is smooth throughout said range of distal movement;

a first liquid medicine disposed in the first medicine chamber; and a second liquid medicine different from the first medicine disposed in the second medicine chamber.

15. The carpule of claim 14, wherein the piston body comprises a cylindrical wall, and wherein the membrane is thin compared to the cylindrical wall.

16. The carpule of claim 14, wherein the first medicine is an anesthetic without a vasoconstrictor and the second medicine is an anesthetic with a vasoconstrictor.

17. The carpule of claim 14, wherein the piston cylindrical body is generally rigid.

* * * * *